United States Patent
Hu et al.

(10) Patent No.: US 10,762,626 B2
(45) Date of Patent: Sep. 1, 2020

(54) ACTIVITY IMAGE RECONSTRUCTION USING ANATOMY DATA

(71) Applicant: Siemens Medical Solutions USA, Inc., Malvern, PA (US)

(72) Inventors: Jicun Hu, Knoxville, TN (US); Vladimir Y. Panin, Knoxville, TN (US); Vijay Shah, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 137 days.

(21) Appl. No.: 16/167,819

(22) Filed: Oct. 23, 2018

(65) Prior Publication Data
US 2020/0126214 A1  Apr. 23, 2020

(51) Int. Cl.
*G06T 7/00* (2017.01)
*G06T 7/11* (2017.01)
*A61B 6/03* (2006.01)
*G06K 9/66* (2006.01)

(52) U.S. Cl.
CPC ............ *G06T 7/0012* (2013.01); *A61B 6/032* (2013.01); *G06K 9/66* (2013.01); *G06T 7/11* (2017.01)

(58) Field of Classification Search
CPC ......... G06T 7/0012; G06T 7/11; A61B 6/032; G06K 9/66
USPC ........................................................ 382/131
See application file for complete search history.

(56) References Cited

U.S. PATENT DOCUMENTS

| | | | | |
|---|---|---|---|---|
| 2006/0127309 A1* | 6/2006 | Raffel | .................. | C07C 279/06 424/1.11 |
| 2006/0269130 A1* | 11/2006 | Maroy | .................... | G06T 7/143 382/173 |
| 2014/0270443 A1* | 9/2014 | Vija | ....................... | A61B 6/037 382/131 |
| 2018/0025512 A1* | 1/2018 | Zhu | ....................... | G06T 11/006 382/131 |
| 2018/0260951 A1 | 9/2018 | Yang et al. | | |
| 2018/0260957 A1 | 9/2018 | Yang et al. | | |
| 2019/0325619 A1* | 10/2019 | Zhang | .................... | G06T 11/008 |

OTHER PUBLICATIONS

Baete, K., et al. "Anatomical-Based FDG-PET Reconstruction for the Detection of Hypo-Metabolic Regions in Epilepsy," IEEE Transactions on Medical Imaging, IEEE Service Center, Piscataway, NJ, USA, vol. 23, No. 4, Apr. 2004, pp. 510-519.
Hi, Jicun, et al. "Clinical Whole Body CBM Parametric PET with Flexible Scan Modes," 2017 IEEE Nuclear Science Symposium and Medical Imaging Conference, Oct. 21, 2017, pp. 1-4.
International Search Report for Corresponding International Patent Application No. PCT/US2019/042312, dated Oct. 9, 2019.

(Continued)

*Primary Examiner* — Michael R Neff

(57) ABSTRACT

A method for reconstructing medical images comprises: identifying a plurality of organs in a body of a subject based on an anatomic image; assigning a plurality of voxels in the body to respective ones of the plurality of organs based on the anatomic image; and reconstructing activity images of the body using respectively different processing for the voxels assigned to each respective one of the plurality of organs.

16 Claims, 14 Drawing Sheets

(56) References Cited

OTHER PUBLICATIONS

Wang, Guobao et al., "Dynamic PET of Human Liver Inflammation: Impact of Kinetic Modeling with Optimization-Derived Dual-Blood Input Function" Phys. Med. Biol., 2018, vol. 63, DOI: 10.1088/1361-6560/aac8cb, pp. 1-14.

Germino, Mary et al., "Cardiac-gated parametric images from 82Rb PET from dynamic frames and direct 4D reconstruction", Med. Phys. 45 (2), Feb. 2018, pp. 639-654.

Yang, Dong, et al., "Automatic Liver Segmentation Using an Adversarial Image-to-Image Network" arXiv:1707.08037v1, Jul. 25, 2017, pp. 1-8.

Wang, Guobao and Qi, Jinyi, "Acceleration of the direct reconstruction of linear parametric images using nested algorithms" Phys. Med. Biol., 55 (2010), pp. 1505-1517.

Ghesu, Florin C., et al., "Multi-Scale Deep Reinforcement Learning for Real-Time 3D-Landmark Detection in CT Scans" IEEE Transactions on Pattern Analysis and Machine Intelligence, Dec. 2017,10.1109/TPAMI.2017.2782687, pp. 1-14.

Chan, Chung et al., "Regularized image reconstruction with an anatomically adaptive prior for positron emission tomography" Phys. Med. Biol., 54 (2009), pp. 7379-7400.

"Nuclear Medicine" http://nibib.nih.gov/science-education/science-topics/nuclear-medicine, printed Aug. 14, 2018, 4 pgs.

Fornell, Dave "SPECT Scanner vs. PET, Which is Best?" https://www.dicardiology.com/article/spect-scanner-vs-pet-which-best, Sep. 3, 2008.

Cheng-Liao, Jinxiu and Qi, Jinyi "PET Image Reconstruction with Anatomical Edge Guided Level Set Prior" Phys. Med. Biol., Nov. 7. 2011; 56(21): pp. 6899-6918.

Gupta, Vineet et al., "A Unified Approach to Adaptive Regularization in Online and Stochastic Optimization" arXiv:1706.06569v1, Jun. 21, 2017, pp. 1-16.

Karakatsanis, Nicolas A., et al., "Whole-body direct 4D parametric PET imaging employing nested generalized Patlak expectation—maximization reconstruction" Phys. Med. Biol., 61 (2016), pp. 5456-5485.

Karakatsanis, Nicolas A., et al., "Generalized whole-body Patlak parametric imaging for enhanced quantification in clinical PET" Phys. Med. Biol., Nov. 21, 2015, 60(22), pp. 8643-8673.

Hutchcroft, Will et al., "Anatomically-aided PET reconstruction using the kernel method" Phys. Med. Biol., 61 (2016), pp. 6668-6683.

\* cited by examiner

ACTIVITY IMAGE RECONSTRUCTION USING ANATOMY DATA

FIELD

This disclosure is related to medical imaging generally, and more specifically to systems combining functional imaging with anatomical imaging techniques.

BACKGROUND

Positron emission tomography (PET) allows detection of cancer and heart disease. PET is considered a functional imaging method, because PET images can show the concentration of a radiotracer in different regions of the imaged organ over the course of time. The radiotracer is injected into the patient at a known location (e.g., the aorta). Sensors (e.g., silicon photomultipliers, SiPM) detect annihilation of positron pairs at various locations over time. The annihilation events indicate the blood flow and radiotracer uptake in the tissue of interest.

Compared to spatial anatomic images (e.g., computed tomography, CT or magnetic resonance imagery, MRI), PET images have lower spatial resolution, lower signal to noise ratio, and can appear more blurry. Also, PET images are captured over a longer period of time, and may have artifacts due to patient motion. As a result, the boundaries between organs in CT and MR images are sharper than PET images.

Many medical imaging systems incorporate spatial information from CT or MR imaging into PET image reconstruction to better define anatomical boundaries and improve image quality.

SUMMARY

In some embodiments, a method for reconstructing medical images comprises: identifying a plurality of organs in a body of a subject based on an anatomic image; assigning a plurality of voxels in the body to respective ones of the plurality of organs based on the anatomic image; and reconstructing activity images of the body using respectively different processing for the voxels assigned to each respective one of the plurality of organs.

In some embodiments, a system for reconstructing medical images comprises a non-transitory, machine-readable storage medium coupled to receive medical image data. The machine-readable storage medium contains instructions. A processor is coupled to the machine-readable storage medium for executing the instructions. The instructions configure the processor for performing a method comprising: identifying a plurality of organs in a body of a subject based on an anatomic image; assigning a plurality of voxels in the body to respective ones of the plurality of organs based on the anatomic image; and reconstructing activity images of the body using respectively different processing for the voxels assigned to each respective one of the plurality of organs.

In some embodiments, a non-transitory, machine-readable storage medium contains instructions, such that when a processor executes the instructions, the instructions configure the processor for reconstructing medical images by: identifying a plurality of organs in a body of a subject based on an anatomic image; assigning a plurality of voxels in the body to respective ones of the plurality of organs based on the anatomic image; and reconstructing activity images of the body using respectively different processing for the voxels assigned to each respective one of the plurality of organs.

DETAILED DESCRIPTION

This description of the exemplary embodiments is intended to be read in connection with the accompanying drawings, which are to be considered part of the entire written description.

A single static or dynamic positron emission tomography (PET) image reconstruction algorithm can be applied to reconstruct an entire volume (e.g., the patient's whole torso, or the patient's torso and head). This may include applying uniform regularization strength throughout the image, and using a uniform Patlak model among all organs in the image.

Embodiments described herein apply organ-based regularization or organ-based kinetic models in static/parametric image reconstruction based on an anatomy map. In some embodiments, an anatomy map can be used to adaptively regularize emission image reconstruction. For example, the anatomy map can assign each voxel to a respective organ, and each organ can have a respective regularization strength (e.g., 0%, 100%, or a value between 0% and 100%) for image reconstruction. Alternatively, the anatomy map can assign each voxel to a respective organ, and assign each organ to a respective kinetics model. The PET images can be reconstructed by applying the respective kinetics model corresponding to each voxel, according to the anatomy map.

In some embodiments, as described herein, the reconstruction parameters or algorithms can be adapted according to human anatomy. Different organs have different physiology and anatomy structures. In dynamic reconstruction, different organs may follow different kinetics models. For example, in brain imaging, anatomy prior may be different depending on whether computed tomography (CT) information or magnetic resonance (MR) information is used. For example, in point spread function (PSF) reconstruction, different widths of PSF can be applied in the brain area and torso region, respectively. In maximum a posteriori (MAP) image reconstruction, different regularization strengths may be applied to different organs, respectively.

Incorporating the anatomy map into activity image reconstruction can provide a more intelligent reconstruction algorithm. For example, reconstruction can apply the anatomy prior, if the organ to be imaged has good correlation with anatomy image or not. In MR/PET, using the T1 image, the anatomy prior can be applied in MR/PET. In PET/CT brain imaging one can turn off anatomy prior.

Figure 13:
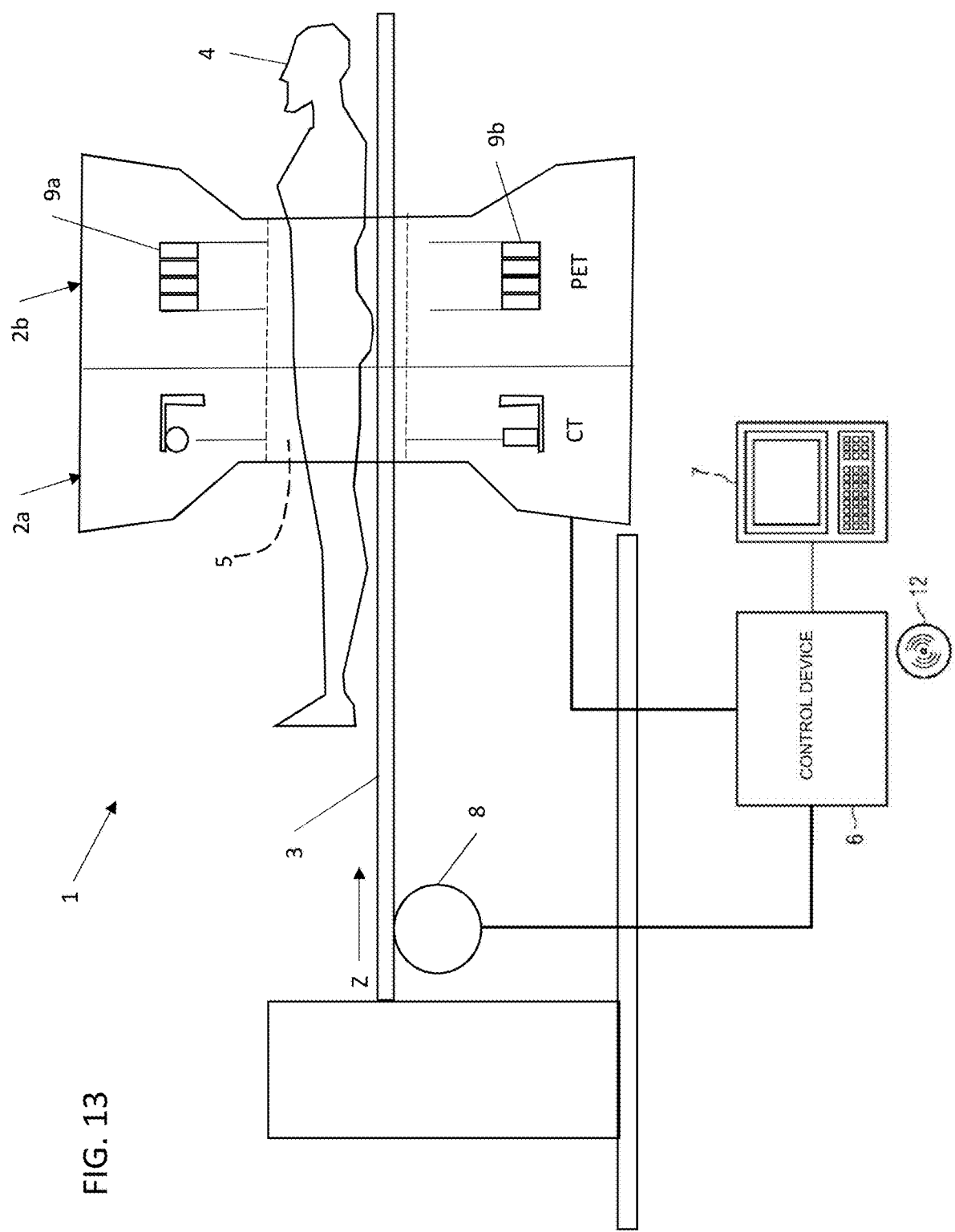
FIG. 13 is a schematic diagram of an apparatus for PET/CT scanning.

FIG. 13 shows a schematic diagram of a medical imaging system 1. In some embodiments, the system 1 includes an anatomy image scanner 2a and an activity (emission) image scanner 2b. The anatomy image scanner 2a can be a computed tomography (CT) or magnetic resonance (MR) scanner. The activity (emission) image scanner 2a can be a positron emission tomography (PET) scanner or a single-photon emission computerized tomography (SPECT) scanner. The system 1 comprises: an examination table 3 for a patient 4 who can be moved on the examination table 3 through an opening 5 of the scanners 2a, 2b, a control device 6, a processor 7 and a drive unit 8. The control device 6 activates the scanners 2 and receives (from the scanners 2a, 2b) signals which are picked up by the scanners 2a, 2b. The scanner 2a picks up x-rays (if scanner 2a is a CT scanner) or radio waves (if scanner 2a is an MR scanner) With the aid of the scanners 2b gamma radiation can be collected (if scanner 2b is a PET scanner or a SPECT scanner). Also disposed in the scanners 2a, 2b is a ring of detector blocks 9a, 9b (collectively referred to as 9) for acquiring photons which are created by annihilation of electrons and positrons in the detector blocks 9a, 9b. Although only 2 detector blocks 9a, 9b are shown in FIG. 13 for ease of viewing, scanners 2a, 2b can have many detector blocks 9 arranged in a cylinder around the circumference of the scanners 2a, 2b. The control device 6 is further operable to receive signals from the detector blocks 9a, 9b and is capable of evaluating these signals for creating PET or SPECT images. The control device 6 further activates the drive unit 8 in order to move the examination table 3 in a direction Z together with the patient 4 through the opening 5 of the scanners 2a, 2b. The control device 6 and the processor 7 can, for example, comprise a computer system with a screen, a keyboard and a non-transitory, machine readable storage medium 12 (hereinafter, "storage medium") on which electronically-readable control information is stored, which is embodied so that it carries out the method described below when the storage medium 12 is used in conjunction with the processor 7 and the control device 6.

Figure 1B:
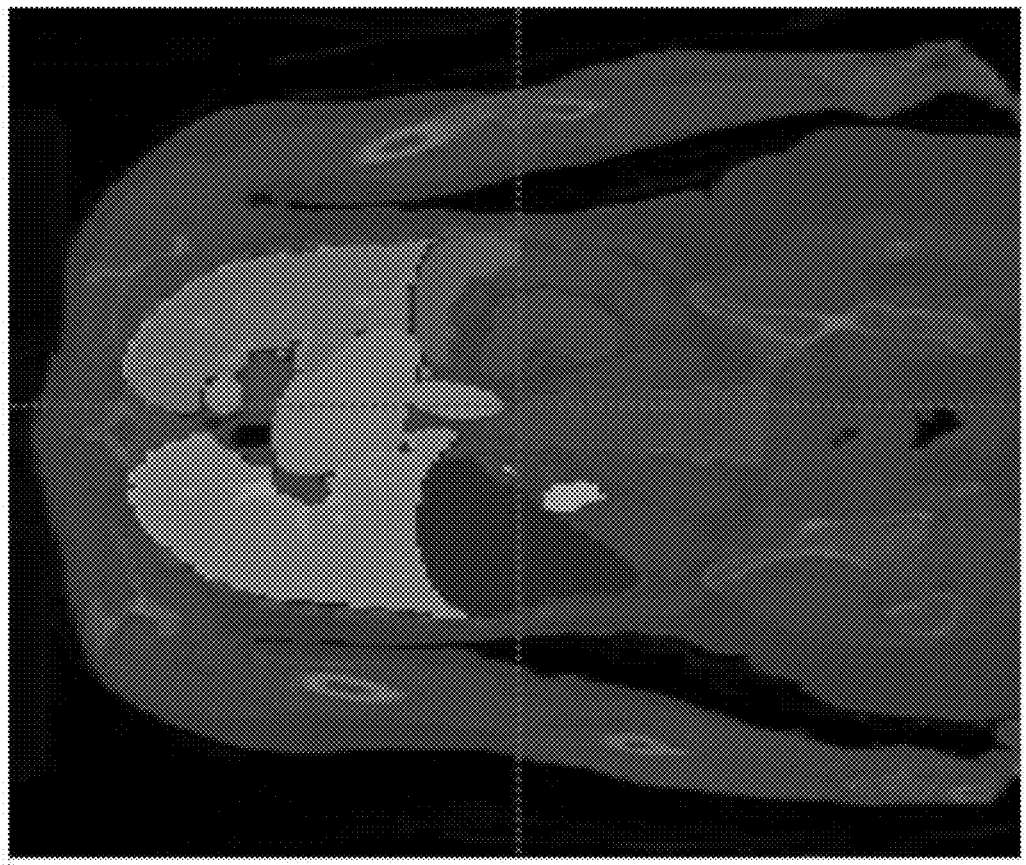
FIG. 1B is a diagram mapping voxels in the segmented anatomy map of FIG. 1A to anatomy data collected from a patient by a computed tomography (CT) scanner.
Figure 1A:
FIG. 1A is a three dimensional (3D) rendering of an anatomy map diagram of a person.

A tool as described in U.S. Patent Application Publication Nos. U.S. 2018/0260951 A1 and US 2018/0260957 A1 by Siemens (both of which are incorporated by reference herein) can be used. The tool is able to accurately segment organs from anatomy images (FIGS. 1A and 1B). The tool is based on an automatic algorithm that detects appropriate landmarks and then segment organs from 3D CT/MR volumes using a deep image-to-image network (DI2IN), employing a convolutional encoder-decoder architecture combined with multi-level feature concatenation and deep super-vision.

The anatomy map in the 3D rendering of FIG. 1A can be overlaid with one or more CT or MR images, as shown in FIG. 1B, so that each voxel of the PET or single-photon emission computerized tomography (SPECT) images can be reconstructed according to the organ to which that voxel is assigned based on the anatomic image data.

After segmentation, each organ may be assigned to an identification table. For example, each organ may be assigned a respective integer (Table 1). The integer numbers corresponding to each organ can be mapped to respective kinetics models, anatomy prior, regularization strength, or the like, or combinations thereof. The anatomy map can comprise a non-transitory, machine-readable storage medium storing a database. In some embodiments, the database can contain a three-dimensional (3D) array, in which each element of the array represents a respective voxel, and contains the identifier (e.g., integer number) representing the organ to which the voxel belongs.

TABLE 1

| Organ | Integer number |
| --- | --- |
| liver | 3 |
| right lung | 4 |
| left lung | 5 |
| left kidney | 6 |
| right kidney | 7 |
| heart | 10 |
| aorta | 11 |
| spleen | 13 |
| brain | 16 |
| bones | 19 |
| remaining organs | 0 |

In some embodiments, each integer number can be used to reference a respective table or table entry defining parameters (e.g., $K_1$, $V_0$) to be used for modeling the organ associated with the integer number. In other embodiments, the model parameters can be incorporated into the segmentation table, so that every voxel has a respective entry with an identifier (e.g., integer number) and a set of kinetics model parameters.

Figure 7A:
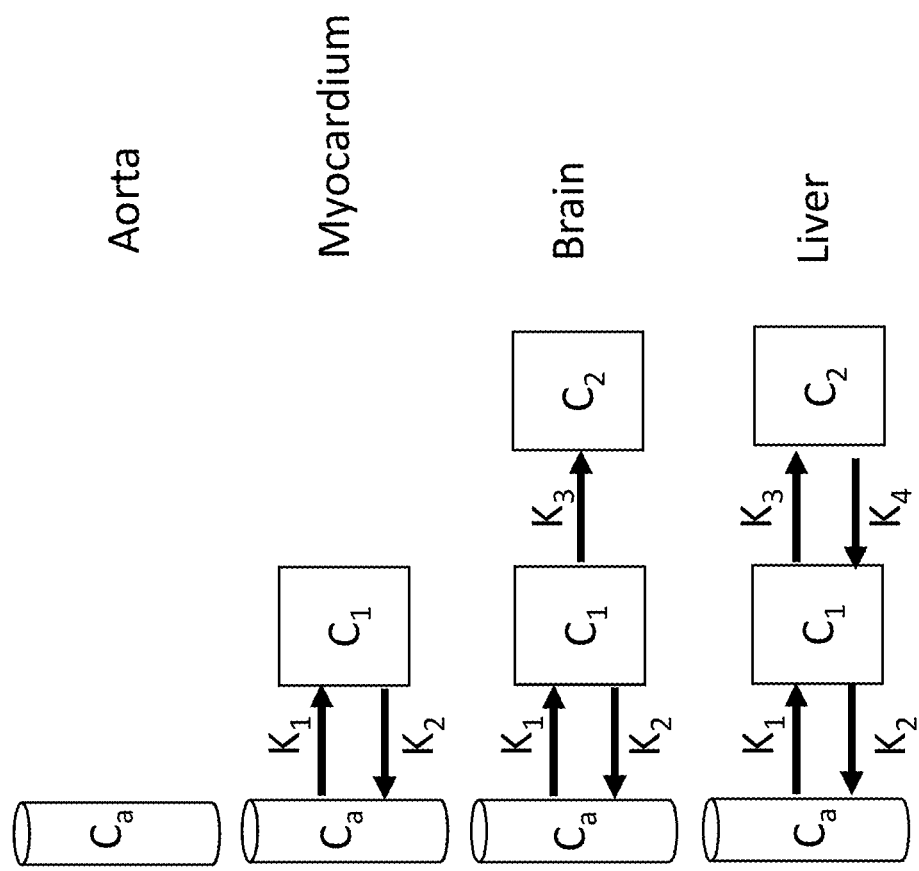
FIG. 7A is a schematic diagram showing different kinetic models for different organs.
Figure 7B:
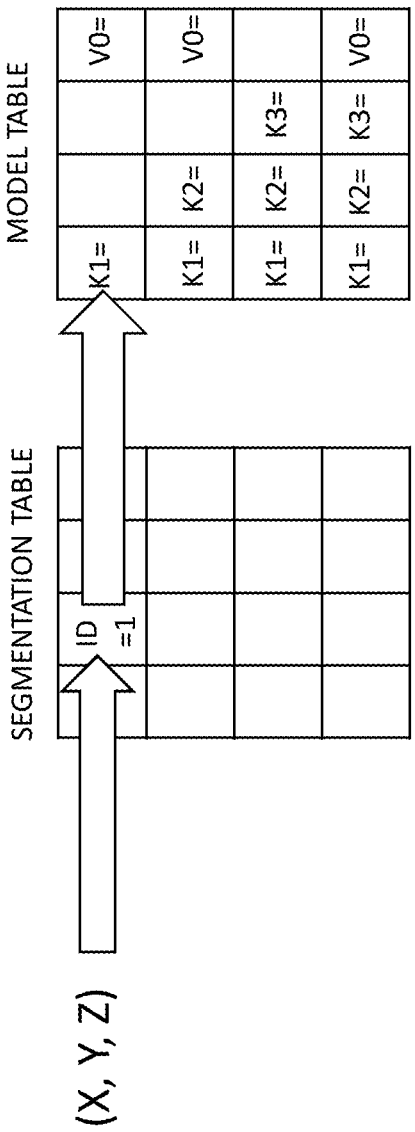
FIG. 7B is a schematic diagram showing a table lookup to determine the applicable kinetic model for a given voxel.
Figure 8:
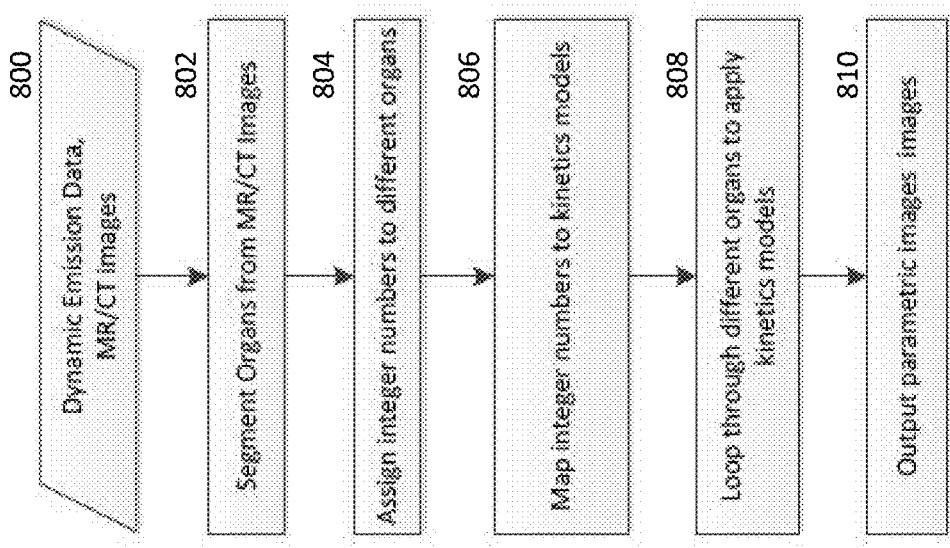
FIG. 8 is a flow chart of a method for applying different kinetic models in reconstructing activity images for different organs.

This anatomy map can guide emission image reconstruction in adaptive regularization (FIG. 2) and/or can use different kinetics models for different organs (FIGS. 7A-8).

Figure 2:
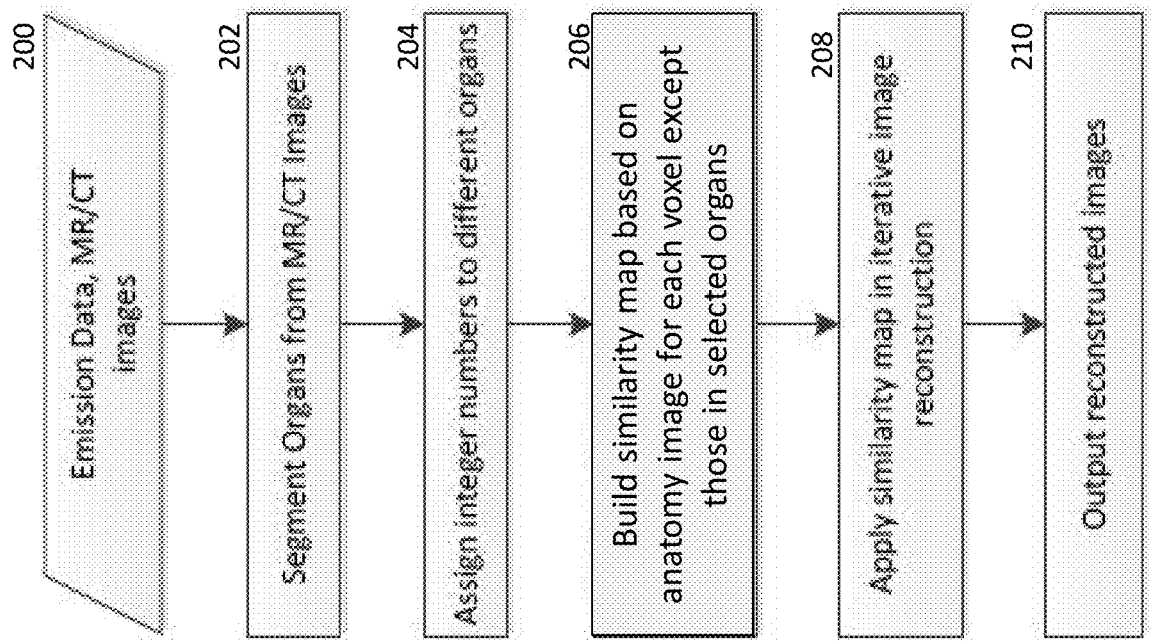
FIG. 2 is a flow chart of a method for applying anatomy data in reconstructing activity images using a similarity map.

Referring first to FIG. 2, in step 200 the emission data are collected. In some embodiments, a single medical imaging system includes an MR scanner or CT scanner for collecting anatomy images, and a PET scanner or SPECT scanner for collecting emission data representing radiotracer concentration. In some embodiments, anatomy and activity data (e.g., PET and CT data) are both collected while the patient remains on the scanner bed, without leaving the bed in between.

At step 202, the anatomy data (MR or CT data) are segmented into organs. Each voxel is identified with a respective organ. For example, the segmenting may be performed using machine learning, with a neural network trained with a set of organs from previous patients identified by trained inspectors. The neural network is trained to classify each voxel as belonging to a particular organ. In other embodiments, the voxels can be assigned to organs using an image recognition algorithm (e.g., feature extraction) or a clustering algorithm.

At step 204, a respective identifier (e.g., integer number) is assigned to each voxel, corresponding to the organ to which that voxel belongs.

At step 206, the system builds a similarity map (according to equations (1) to (4), based on the anatomy (MR or CT) image for each voxel. In some embodiments, the similarity map excludes voxels assigned to one or more organs to which the anatomy prior is not to be applied. For example, in some embodiments, the system determines whether the functional (PET or SPECT) image values are correlated with the anatomical (MR or CT) image values.

The similarity map can be built using a radial Gaussian kernel. The PET image value x at a pixel j,k is given by equation (1):

$$x = K\alpha \quad (1)$$

where the kernel K is defined by equation (2), and $\alpha$ is the coefficient image defined by equation (3).

The kernel function $K(f_j, f_k)$ for each pair of anatomical pixels j and k is defined by equation (2).

$$K(f_j, f_k) = \exp\left(\frac{-\|f_j - f_k\|^2}{\sigma^2}\right) \quad (2)$$

where $f_j$ and $f_k$ are anatomical feature vectors for pixels j and k, respectively, K is a kernel function, and the parameter $\sigma$ controls the edge sensitivity.

For expectation maximization (EM), the coefficient image is defined by equation (3).

$$\alpha^{n+1} = \frac{\alpha^n}{K^T P^T \left(\frac{1}{AN}\right)} \left(K^T P^T \frac{y}{PK\alpha^n + A(NR+S)}\right) \quad (3)$$

where $P \in \mathbb{R}^{M_d \times N_v}$ is the system matrix with $p_{ij}$ denoting the probability of detecting an event originating in voxel j in detector pair i, and r is a vector encompassing random and scattered events, and $M_d$ and $N_v$ represent the number of detector bins and voxels, respectively. A is attenuation correction factor, N is normalization factor, and S is simulated scatter sinogram. The similarity matrix (map) K for a given organ is given by equation (4)

$$K(f_j, f_k) = \exp\left(\frac{-\|f_j - f_k\|^2}{\sigma^2}\right) \text{organ}(f_j) \quad (4)$$

Referring again to FIG. 2, at step 208, the similarity map is applied in iterative image reconstruction, e.g., with the Ordered Subsets Expectation Maximization (OSEM) algorithm in equation (3).

At step 210, the system outputs the reconstructed images.

The anatomy map of FIG. 1B and Table 1 can be used to specifically identify the organs that have good correlation between activity and the attenuation map in building the similarity matrix according to equation (4).

In equation (4), the similarity values with adjacent voxels $f_k$ are calculated for voxels $f_j$ in organs that have good correlation between anatomy and activity, and no similarity values need to be calculated for voxels in organs that do not have good correlation between anatomy and activity. For example, PET and CT data for the brain are known to have poor correlation, so there is no need to calculate similarity values for the voxels in the brain. This adaptive calculation of similarity matrix can be controlled by the factor organ($f_j$) in equation (4) since organ($f_j$) keeps track of which organ voxel $f_j$ belongs to.

Figure 3A:
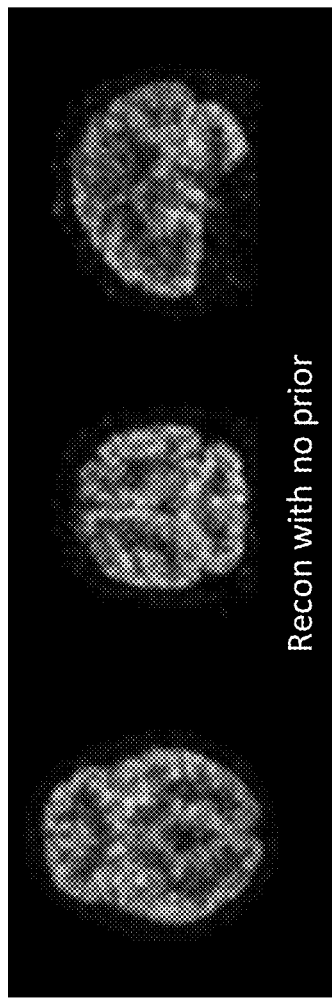
FIGS. 3A-3C show an example applying MR anatomy prior data in reconstructing a brain image.
Figure 3B:
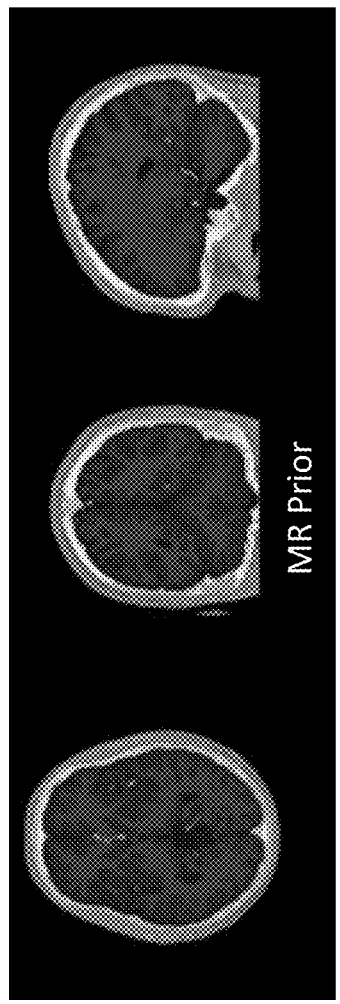
Figure 3C:
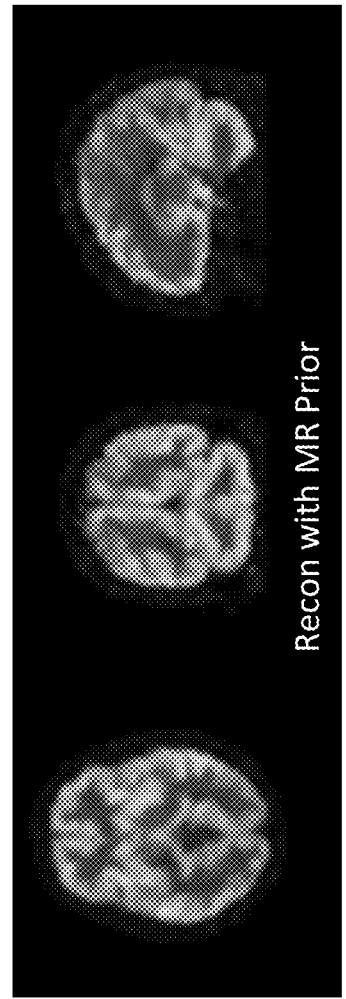

FIGS. 3A-3C show an example where there is good correlation between (functional) PET image reconstruction with no anatomy prior (shown in FIG. 3A) and the MR anatomy prior images of the brain (FIG. 3B). Both FIGS. 3A and 3B show details of the soft tissue of the brain. Consequently, reconstructing the PET image data of FIG. 3A using the anatomy prior information from the MR images in FIG. 3B provides a smoother image, as shown in FIG. 3C. Similarly, there is good correlation between the anatomy and emission information for the torso (not shown in FIGS. 3A-3C), regardless of whether MR or CT data are used for the torso.

Figure 4A:
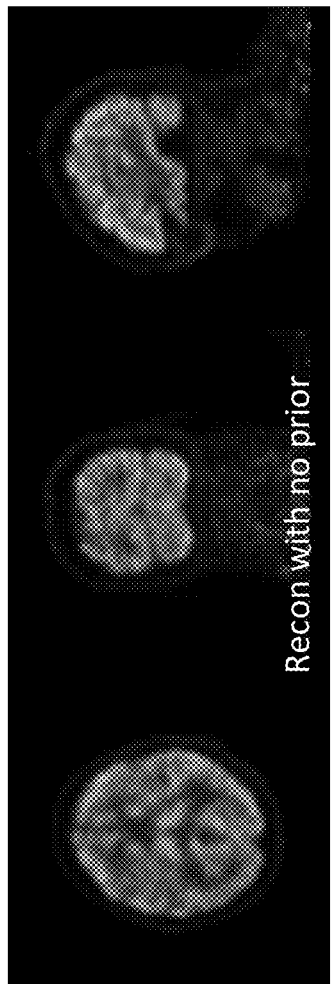
FIGS. 4A-4C show an example applying CT anatomy prior data in reconstructing a brain image.
Figure 4B:
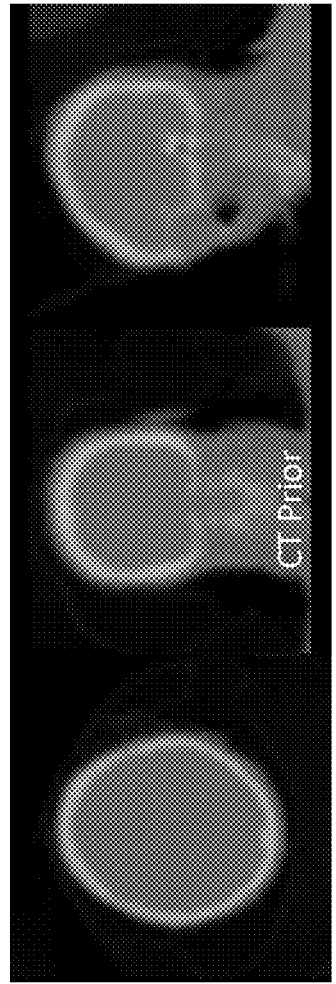
Figure 4C:
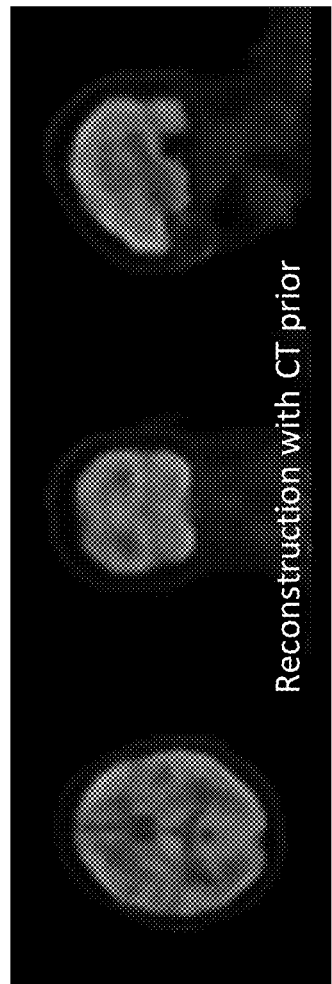

FIGS. 4A-4C show an example where there is poor correlation between (activity) PET image reconstruction of the brain with no anatomy prior (shown in FIG. 4A) and the CT anatomy prior images of the brain (FIG. 4B). FIG. 4A shows details of the soft tissue of the brain, but the CT images in FIG. 4B only show the bone. Consequently, reconstructing the PET image data of FIG. 4A using the anatomy prior information from the CT images in FIG. 4B over-smooths the image, as shown in FIG. 4C, causing loss of detail while reducing noise. Thus, it can be advantageous to exclude CT anatomy prior data for the skull from a similarity map for the brain in step 206 of FIG. 2.

In FIGS. 5A-5D, a similarity matrix was built for all voxels that are located outside of the brain based on the attenuation map. The method distinguishes regions having different attenuation properties, assigning linear attenuation coefficients to them to provide an attenuation map to correct the PET emission data during reconstruction. The attenuation map prior can be successfully applied in the region outside of the brain. The reconstructed brain is not smoothed.

Figures 5A, 5B, 5C, 5D:
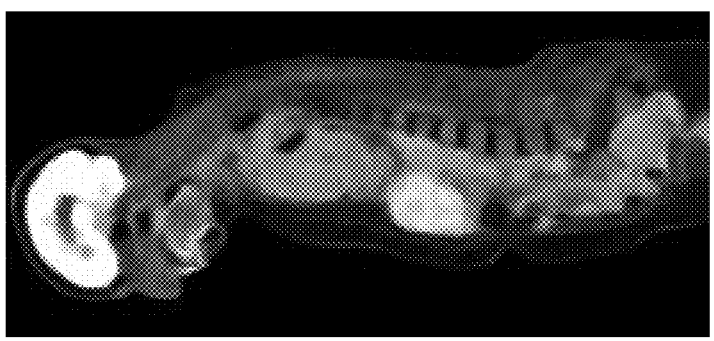
FIGS. 5A-5D show an example adaptively applying CT anatomy prior data in reconstructing a whole body image using a similarity map.

FIG. 5A shows the result of standard uptake value (SUV) reconstruction without using any anatomy prior. The torso portions of the image are noisy.

FIG. 5B shows the PET data from FIG. 5A, reconstructed using anatomy prior data from a corresponding CT image to the torso and the brain. The torso portion of the image is improved by noise reduction while retaining acceptable detail, but detail is lost in the brain portion of the image, since the brain anatomy (CT) data are not correlated with the brain activity (PET) data.

FIG. 5C shows the image reconstructed using the similarity matrix for all voxels located outside the brain. The torso portion of the image benefits from noise reduction, similar to the torso in FIG. 5B, but the brain portion retains detail, similar to the brain portion of FIG. 5A. In this instance, the benefit of retaining detail in the brain in FIG. 5C exceeds the cost of foregoing noise reduction in the brain.

FIG. 5D shows the anatomy map overlaid with the CT data. The anatomy map from MR/CT can be used to design more intelligent reconstruction algorithms by knowing to which organ each voxel belongs.

In various embodiments, the system can selectively and/or variably apply anatomy prior data for reconstruction of PET or SPECT images, depending on the correlation between anatomy and activity data for each individual organ. The system can apply different regularization or anatomy prior to different organs.

In some embodiments, the system can apply different kinetics models to different organs for parametric imaging to increase accuracy and signal to noise ratio.

FIGS. 6A-6D show another example using adaptive regularization strength with quadratic prior. As noted above, it can be advantageous to use MR or CT anatomy prior if the anatomic data and activity data are highly correlated, and it can be advantageous to reconstruct the PET images without using anatomy prior if the anatomic data and activity data have very low correlation. Adaptive regularization strength allows use of reduced regularization strength based on CT anatomy prior for intermediate correlation between anatomic data and activity data. Adaptive regularization can strike a balance between reducing noise and preserving detail.

Figure 6A:
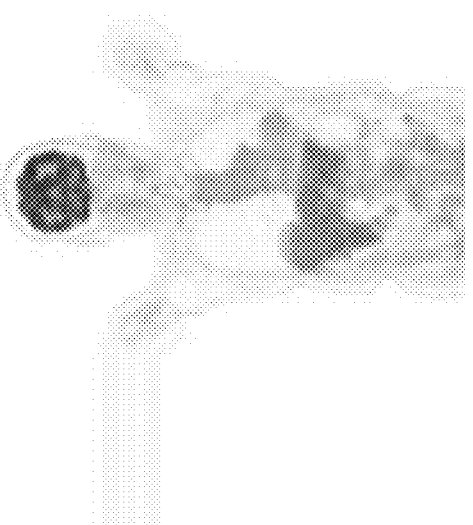
FIGS. 6A-6D show an example applying CT anatomy prior data in reconstructing a whole body image using adaptive regularization.
Figure 6B:
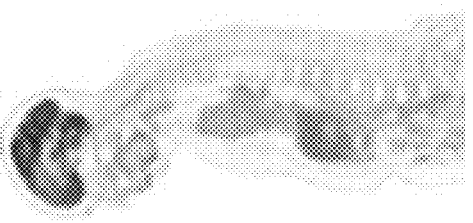
Figure 6C:
Figure 6D:
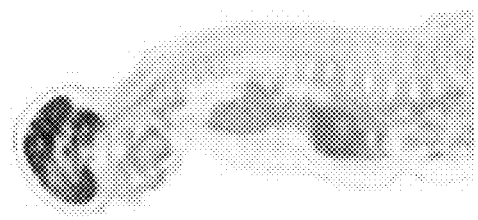

FIGS. 6A and 6B are coronal and sagittal views of a patient reconstructed with uniform regularization strength: 100% regularization strength for the torso (based on the CT data) and 100% regularization strength for the brain (based on the CT data). The brain portion of the image is oversmoothed. FIGS. 6C-6D show another method of reconstructing an image from the same PET data as FIGS. 6A and 6B using adaptive regularization strength. In FIGS. 6C-6D, the regularization strength applied to the brain was one third of that applied to the rest of human body. By using a reduced regularization strength in FIGS. 6C and 6D, better resolution was preserved in the brain region (compared to FIGS. 6A and 6B), while providing an acceptable noise level. This is only one example, and the regularization strength applied to any given organ can be varied to any value between 0% and 100%.

Alternatively, the anatomy map can be applied to parametric imaging. For example, Patlak model may be sufficient for tumor (hot spot) imaging. However, the parametric images (Ki and Dv) are noisy compared to SUV images, and the linear Patlak model may be not accurate for parametric imaging for some organs. In some embodiments, the system can apply different kinetics models to different organs. Applying different kinetic models to different organs may increase signal to noise ratio of parametric images.

In some embodiments, the anatomy map or segmentation table is used to determine to which organ each voxel is assigned, and each organ is assigned to a respective kinetics model. FIGS. 7A and 7B schematically show an indexing method for determining which parameters are included in the kinetics model for a given organ. For example, as shown in FIG. 7B, if the segmentation table record corresponding to a given voxel contains the integer number 1, the model parameters for that voxel are identified in the first entry (e.g., row or column) of the model table. In this case, the first row of the model table indicates that a linear model is used, and the parameters $K_1$ and $V_0$ will be identified, and parametric $K_1$ and $V_0$ images will be reconstructed. Similarly, the remaining entries (rows or columns) of the model table identify the parameters of the models used for other organs.

For example, in some implementations of parametric imaging systems, the Patlak model was applied to all of the voxels in the image. A Patlak model is a linear model based on equation (5):

$$\frac{R(t)}{C_p(t)} = K \frac{\int_0^t C_p(\tau)d\tau}{C_p(t)} + V_0 \quad (5)$$

where R is an amount of tracer in a region of interest, $C_p(t)$ is the concentration of the tracer in blood, K is the rate of entry into the peripheral (irreversible) compartment, and $V_0$ is the distribution volume of the tracer in the central (reversible) compartment.

The model of equation (5) assumes that all voxels follow the linear model regardless of which organ the voxels are in. However, many organs exhibit more complex behavior. For example, FIG. 7A shows four different schematic models for the aorta, myocardium, brain, and liver, respectively. The aorta is considered as a pass-through, with no tracer uptake, and no change in tracer concentration between the inlet to the aorta and exit from the aorta. The myocardium can be modeled as having one reversible compartment C1, with respective constants $K_1$ and $K_2$ defining tracer influx and outflux, respectively. The brain can be modeled as having a reversible compartment $C_1$ and an irreversible compartment $C_2$. The parameter $K_3$ is added, denoting uptake by the irreversible compartment $C_2$. The liver can be modeled as having two reversible compartments $C_1$ and $C_2$. A liver outflux parameter $K_4$ is added.

The anatomy map also allows organ-specific parametric imaging and can increase signal to noise ratio of parametric images. The anatomy map can be derived from high resolution MR or CT images. In static or parametric emission image reconstruction, the correlation information between anatomy (e.g., MR and/or CT) and emission (PET or SPECT) images, allow more accurate kinetics modeling, to de-noise parametric images, and also to provide more desirable correction effects that adapt to clinical needs.

FIG. 8 is a flow chart of a method applying different kinetics models to different organs in dynamic imaging. At step 800, the emission data are collected. In some embodiments, a single medical imaging system includes an MR scanner or CT scanner for collecting anatomy images, and a PET scanner or SPECT scanner for collecting emission data representing radiotracer concentration.

At step 802, the anatomy data (MR or CT data) are segmented into organs. Each voxel is identified with a respective organ. Any segmentation method can be used, such as those discussed above with respect to step 202 of FIG. 2.

At step 804, a respective identifier (e.g., integer number) is assigned to each voxel, corresponding to the organ to which that voxel belongs.

At step 806, the system maps each identifier (e.g., integer number) to a respective kinetics model. For example, the mapping can be as shown in FIG. 7A or FIG. 7B.

At step 808, the method loops through each organ to apply the respective kinetics model corresponding to each voxel.

At step 810, the system outputs parametric images for each of the model parameters.

Figure 9:
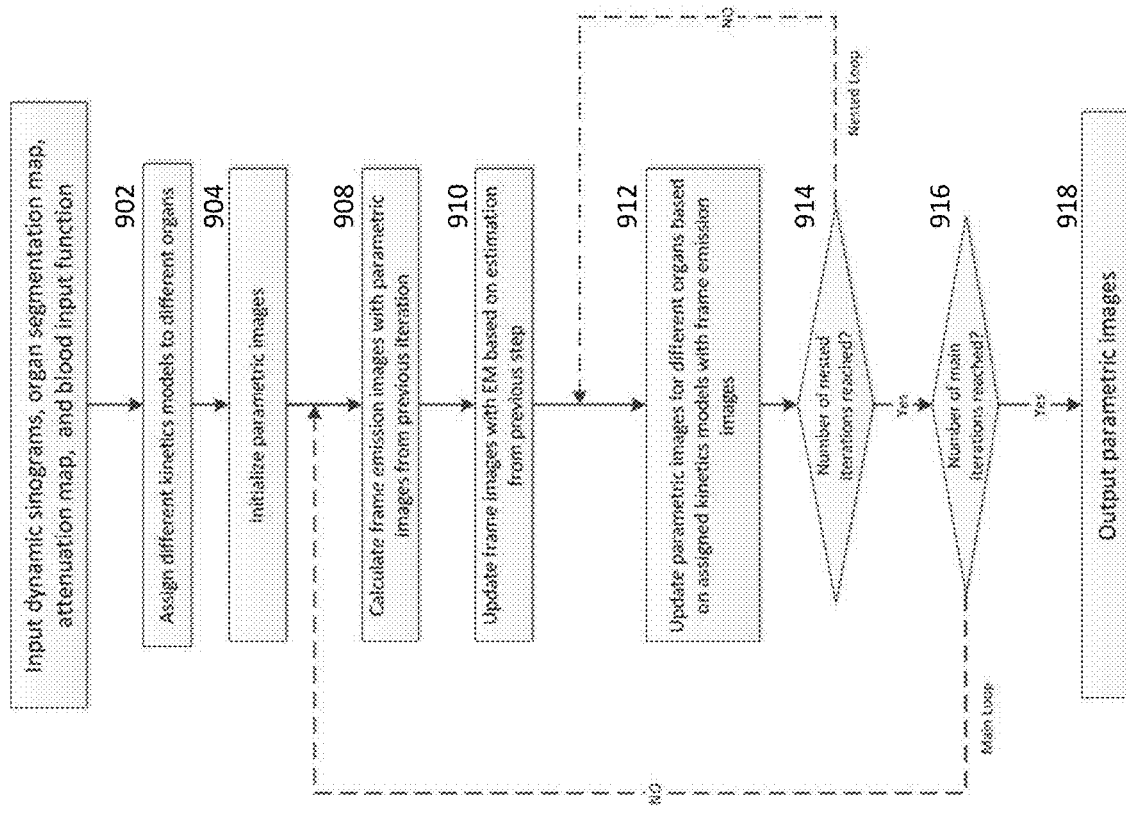
FIG. 9 is a flow chart of an embodiment of a method for applying different kinetic models in reconstructing activity images for different organs.

FIG. 9 shows an exemplary embodiment for applying different kinetic models to respective organs.

At step 900, the dynamic sinogram data, organ segmentation map, attenuation map, and the blood input function are input to the system. In some embodiments, the sinogram data and organ segmentation map can be captured using a scanner having a PET or SPECT acquisition scanner and a CT or MRI scanner. In other embodiments, the sinogram data and organ segmentation map can be previously stored data accessed from a non-transitory, machine-readable storage medium.

Figure 10:
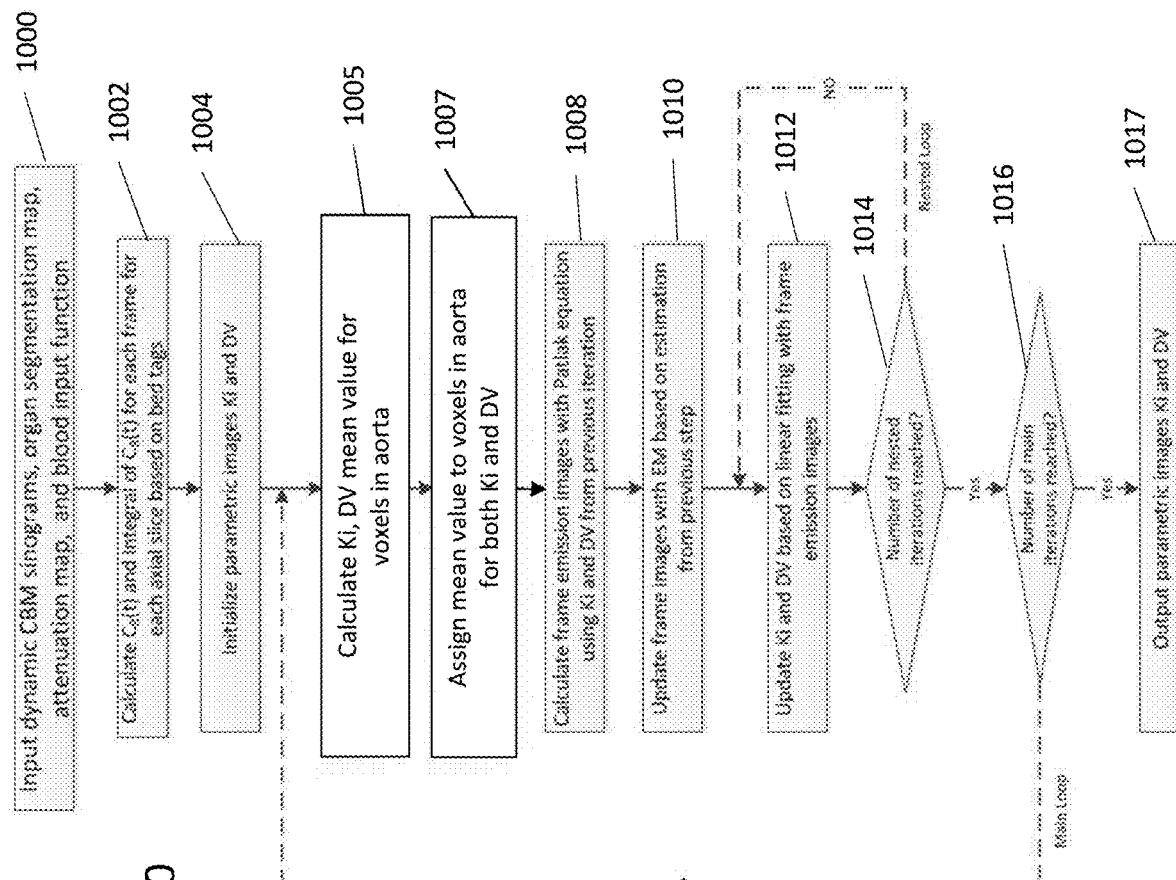
FIG. 10 is a flow chart of an embodiment of an example of the method of FIG. 9.

At step 902, each organ is assigned to a respective kinetics model. For simplicity, the remaining steps in FIG. 10 are based on a linear Patlak model, but in other examples, one or more other models, such as multi-compartment models and/or non-linear models are used.

At step 904, each parametric image is initialized. For example, all voxels for each parametric image can initially be set to a uniform value (e.g., all black, all white, or all gray).

Steps 908 to 916 perform the main loop.

At step 908, the system calculates frame emission images using expectation maximization. The frame emission images include a respective SUV image for each time point at which the sinogram data are collected. The first time step 908 is performed, the frame emission images are calculated using the initial parameter values from step 904. Subsequently, each iteration of step 908 is performed using the parametric images from the previous iteration of the main loop.

At step 910, each frame image (SUV image corresponding to each collection time point during the scan) is updated based on the estimation from the previous time step. For example, the frame image corresponding to the second time point is updated based on the frame image corresponding to the first time point.

Steps 912 and 914 form an inner loop to perform kinetic modeling. The inner loop updates the parametric images based on the frame images.

Step 912 updates parametric images (e.g., the Ki an Dv images) for an organ based on its respective assigned kinetics model using the frame emission images. For each voxel, a line or curve (depending on the respective model assigned to each organ) is fit to the frame image data for that voxel over all of the time points, and the parameter values (e.g., Ki and Dv) are determined.

At step 914, the updates to the parametric images in step 912 are repeated for each organ.

At step 916, the main loop from step 908 to 916 is repeated until a desired number of iterations have been performed.

At step 918, once the desired number of iterations are performed, the respective parametric images for each organ are output.

FIG. 10 shows an exemplary embodiment for applying different kinetic models to respective organs, where the organs include at least the aorta.

At step 1000, the dynamic sinogram data, organ segmentation map, attenuation map, and the blood input function are input to the system. In some embodiments, the scanner is operated in continuous bed motion (CBM) mode. In other embodiments, step-and-scan mode is used. In some embodiments, the sinogram data and organ segmentation map can be captured using a scanner having a PET or SPECT acquisition scanner and a CT or MRI scanner. In other embodiments, the sinogram data and organ segmentation map can be previously stored data accessed from a non-transitory, machine-readable storage medium.

At step 1002, the system calculates the blood tracer concentration $C_B(t)$ and the integral of $C_B(t)$ for each time point, for each axial slice of the scan. In some embodiments, the method to calculate image slice reference time of different scan passes for parametric PET are based on finely sampled "bed tags". Bed tags are coordinate pairs accurately encoding position and time information of the bed throughout the scan. In a system scanning in CBM mode, bed tags can be recorded periodically, providing an accurate record of position versus time regardless of bed speed and acceleration. In other embodiments, the system scans in step-and-shoot mode.

At step 1004, each parametric image (e.g., Ki and DV) is initialized. For example, all voxels for each parametric image can initially be set to a uniform value (e.g., all black, all white, or all gray).

Steps 1005 to 1016 perform the main loop.

Steps 1005 and 1007 constitute a regularization step. At step 1005 the system calculates the mean parameter values for each parameter (e.g., Ki, DV) for the voxels in each organ. In the example of FIG. 10, the mean parameter values are assigned for the aorta. Ki and DV are calculated for each voxel using equations (6) and (7), respectively:

$$k_{ij} := \frac{K_{i_j}}{\Sigma_t \int_0^t c_p(\tau) d\tau} \Sigma_t \int_0^\tau c_p(\tau) d\tau \frac{x_j(t)}{x_j(t, K_{i_j}, DV_j)} \quad (6)$$

$$DV_j := \frac{DV_j}{\Sigma_t c_p(t)} \Sigma_t c_p(t) \frac{x_j(t)}{x_j(t, K_{i_j}, DV_j)} \quad (7)$$

if voxel j belongs to aorta in anatomy map, the means are calculated by:

$K_{ij}$=mean($K_{ij}$(aorta))

$DV_k$=mean($DV_j$(aorta))

At step 1007, the mean parameter values computed over all the voxels is assigned to each voxel in each organ. In the example of FIG. 10, each voxel is set to the mean parameter values Ki and DV computed in step 1005.

At step 1008, the system calculates frame emission images using (the Patlak) equation (8).

$$x_j(t, K_{i_j}, DV_j) = K_{i_j} \int_o^t C_p(\tau) d\tau + DV_j C_p(t) \quad (8)$$

The frame emission images include a respective SUV image for each time point at which the sinogram data are collected. The first time step 1008 is performed, the frame emission images are calculated using the initial parametric images from step 1004. Subsequently, each iteration of step 1008 is performed using the parametric images from the previous iteration of the main loop (steps 1005-1016).

At step 1010, each frame image (SUV images corresponding to each collection time point during the scan) is updated based on the estimation from step 1008. The updates are performed according to equation (9)

$$x_j(t) := \frac{x_j(t, K_{i_j}, DV_j)}{n_j(t)} \Sigma_l p_{lj} \frac{y_l(t)}{\Sigma_j p_{lj} x_j(t, K_{i_j}, DV_j) + o_l(t)} \quad (9)$$

Steps 1012 and 1014 form an inner loop to perform kinetic modeling.

Step 1012 updates parametric images (e.g., the Ki an Dv images) for an organ based on its respective assigned kinetics model using the frame emission images. For each voxel, a line or curve is fit to the frame image data for that voxel over all of the time points, and the parameter values (e.g., Ki and Dv) are determined.

At step 1014, the updates to the parametric images in step 1012 are repeated for each organ.

At step 1016, the main loop from step 1008 to 1016 is repeated until a desired number of iterations have been performed.

At step 1017, once the desired number of iterations are performed, the processor outputs Ki and DV parametric images.

FIGS. 11A-11E compare parametric images of the same subject before and after application of the aorta anatomy map.

Figure 11C:
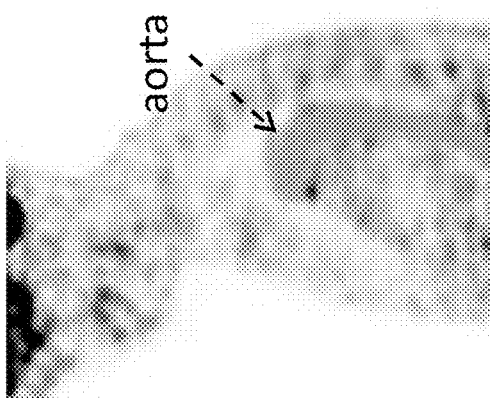
FIGS. 11A-11E show application of CT data for parametric images of the aorta.
Figure 11E:
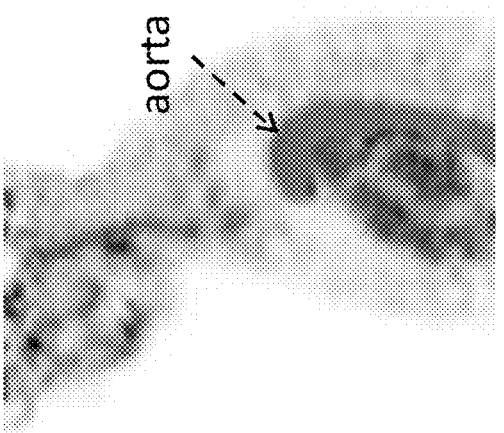
Figure 11B:
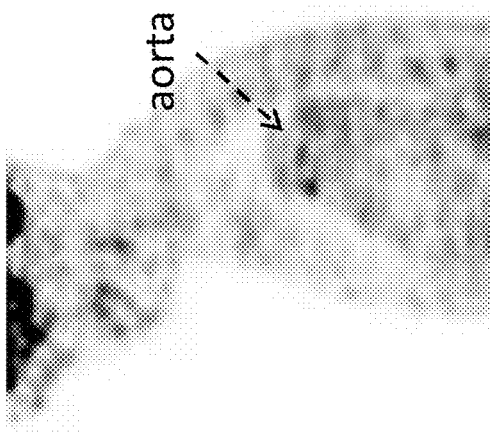
Figure 11D:
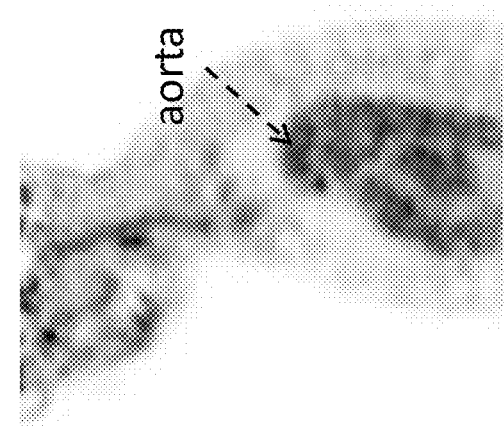
Figure 11A:
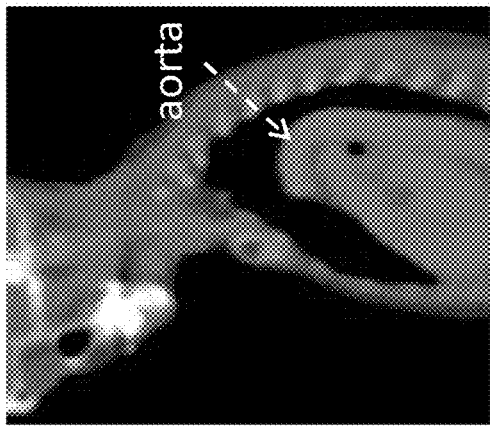

FIG. 11A shows a sagittal view CT image of the subject. The aorta is labeled and is readily distinguished from surrounding organs. The CT image of FIG. 11A has low noise.

FIG. 11B shows the sagittal view Ki parametric image of the same subject, without applying the aorta map information of FIG. 11A. The aorta is labeled in FIG. 11B, but the image contains a large amount of noise.

FIG. 11C shows the sagittal view Ki parametric image of the same subject, after applying the aorta map information of FIG. 11A. The aorta is labeled in FIG. 11C. Noise is substantially reduced relative to FIG. 11B, and the image quality of the aorta is improved.

FIG. 11D shows the sagittal view DV parametric image of the same subject, without applying the aorta map information of FIG. 11A. The aorta is labeled in FIG. 11D. The image contains a large amount of noise.

FIG. 11E shows the sagittal view DV parametric image of the same subject, after applying the aorta map information of FIG. 11A. The aorta is labeled in FIG. 11E. Noise is substantially reduced, and the image quality of the aorta is improved.

FIGS. 12A-12D show a similar improvement in parametric images of the liver obtained by applying the liver map to PET parametric image processing.

Figure 12A:
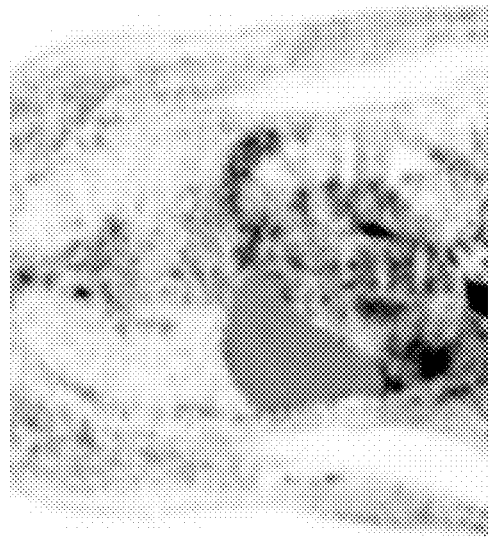
FIGS. 12A-12D show application of CT data for parametric images of the liver.

FIG. 12A shows the anterior view Ki parametric image of the subject, without applying the liver map. The liver is labeled in FIG. 12A, but the image contains a large amount of noise.

Figure 12B:
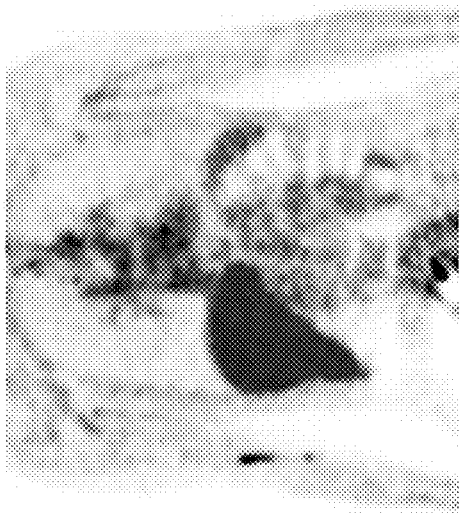

FIG. 12B shows the sagittal view Ki parametric image of the same subject, after applying the liver map information. The liver is labeled in FIG. 12B. Noise is substantially reduced relative to FIG. 12A, and the image quality of the liver is improved.

Figure 12C:
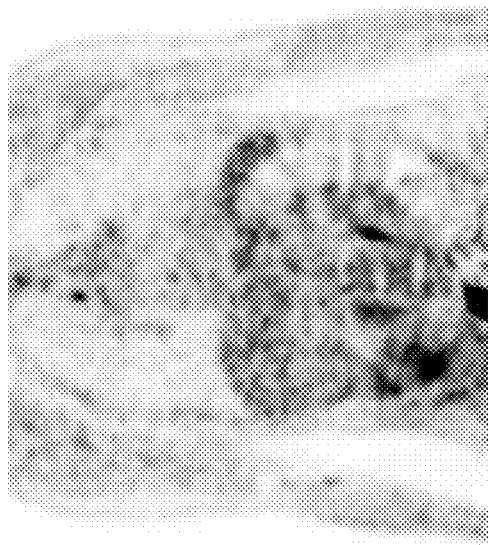

FIG. 12C shows the anterior view DV parametric image of the subject, without applying the liver map. The liver is labeled in FIG. 12C, but the image contains a large amount of noise.

Figure 12D:
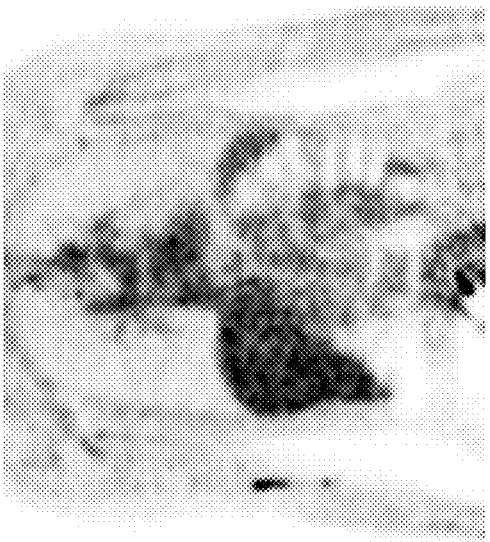

FIG. 12D shows the sagittal view DV parametric image of the same subject, after applying the liver map information. The liver is labeled in FIG. 12D. Noise is substantially reduced relative to FIG. 12C, and the image quality of the liver is improved.

Thus, the signal to noise ratio in the aorta or liver region of parametric images can be improved by including the anatomy information of the aorta or liver (or other organ of interest) in the nested Patlak image reconstruction. The techniques described above can be applied to parametric imaging of other organs.

The anatomy map can also be used in other data correction methods, such as motion correction, scatter correction, and point spread function. In various embodiments, the anatomy map can also be used for the following aspects, either alone, or in any combination:

(a) Applying respectively different regularization strength over different organs in maximum a posterior (MAP) image reconstruction;

(b) Applying data correction algorithms adaptively. For example, we can turn off point spread function (PSF) off in the brain protocol and turn on PSF in the whole body protocol. The system can apply different correction methods (e.g., point spread function, scatter scaling) to different regions of the human body.

(c) Applying different PSF width to different parts of the human body. For example, for the brain, the method can use a smaller point spread function, and for the torso region, use a larger width of the point spread function. The radiologist can use a smaller width of point spread function for regions with large amounts of detail (e.g., the brain) to see less blurring in the brain. For the torso, the radiologist can apply a point spread function with a larger width to reduce noise where there is less detail, and reduce noise more.

(d) Applying motion correction more intelligently. For motion correction, once the segmentation map is obtained, the system can associate every voxel with the correct organ to which it belongs. The system can apply motion correction for voxels in organs likely to have motion, and omit motion correction for organs which are less likely to have motion. For example, if the patient 4 is stationary on the bed 3, the brain does not have much motion, but the lung and heart have substantial motion during respiration, so the system can apply motion correction to the voxels assigned to organs in the torso (e.g., lung and heart), but not use motion correction for voxels assigned to the brain.

(e) Applying anatomy information regarding lesions. If lesion information is available, the system can include lesion information in the anatomy map, and can reconstruct image region better. For example, the lesion (e.g., malignant tumor) can be treated as a separate organ in the anatomy map, and the system can apply a kinetic model to the lesion different from the kinetic model used for the organ on which the lesion is located. The system can thus obtain more accurate blood activity information with respect to the lesion.

The methods and system described herein may be at least partially embodied in the form of computer-implemented processes and apparatus for practicing those processes. The disclosed methods may also be at least partially embodied in the form of tangible, non-transitory machine readable storage media encoded with computer program code. The media may include, for example, RAMs, ROMs, CD-ROMs, DVD-ROMs, BD-ROMs, hard disk drives, flash memories, or any other non-transitory machine-readable storage medium, wherein, when the computer program code is loaded into and executed by a computer, the computer becomes an apparatus for practicing the method. The methods may also be at least partially embodied in the form of a computer into which computer program code is loaded and/or executed, such that, the computer becomes a special purpose computer for practicing the methods. When implemented on a general-purpose processor, the computer program code segments configure the processor to create specific logic circuits. The methods may alternatively be at least partially embodied in a digital signal processor formed of application specific integrated circuits for performing the methods.

Although the subject matter has been described in terms of exemplary embodiments, it is not limited thereto. Rather, the appended claims should be construed broadly, to include other variants and embodiments, which may be made by those skilled in the art.

What is claimed is:

1. A method for reconstructing medical images, comprising:
 identifying a plurality of organs in a body of a subject based on an anatomic image;
 assigning a plurality of voxels in the body to respective ones of the plurality of organs based on the anatomic image; and reconstructing activity images of the body using respectively different processing for the voxels assigned to each respective one of the plurality of organs, wherein the reconstructing includes performing regularization for one or more selected organs based on information from the anatomic image and wherein the reconstructing includes performing regularization for one or more selected organs based on information from the anatomic image.

2. The method of claim 1, wherein the anatomic image is a computed tomography (CT) image or a magnetic resonance (MR) image of the body, and the activity images are positron emission tomography (PET) or single-photon emission computerized tomography (SPECT) images.

3. The method of claim 1, wherein the anatomic image is a CT image, the activity images are PET images, and the reconstructing includes:
using information from the anatomic image to reconstruct a portion of the anatomic image containing a brain; and
reconstructing a portion of the image containing an organ within a torso of the body without information from the anatomic image.

4. The method of claim 1, wherein the regularization is performed adaptively based on the organ to which each voxel is assigned.

5. The method of claim 1, further comprising applying respectively different kinetic models to voxels assigned to respectively different ones of the plurality of organs.

6. The method of claim 1, further comprising applying respectively different image corrections to voxels assigned to respectively different ones of the plurality of organs.

7. The method of claim 6, wherein the respectively different image corrections include respectively different point spread functions.

8. The method of claim 6, wherein the respectively different image corrections include respectively different scatter scaling.

9. The method of claim 6, wherein the respectively different image corrections include respectively different motion correction.

10. A system for reconstructing medical images, comprising:
a non-transitory, machine-readable storage medium coupled to receive medical image data, the machine-readable storage medium containing instructions; and
a processor coupled to the machine-readable storage medium for executing the instructions, wherein the instructions configure the processor for performing a method comprising:
identifying a plurality of organs in a body of a subject based on an anatomic image;
assigning a plurality of voxels in the body to respective ones of the plurality of organs based on the anatomic image; and
reconstructing activity images of the body using respectively different processing for the voxels assigned to each respective one of the plurality of organs, wherein the reconstructing includes performing regularization for one or more selected organs based on information from the anatomic image and wherein the selected organs are selected based on a correlation between voxel values of the anatomic image and voxel values of the activity images.

11. The system of claim 10, wherein the anatomic image is a CT image, the activity images are PET images, and the reconstructing includes:
using information from the anatomic image to reconstruct a portion of the anatomic image containing a brain; and
reconstructing a portion of the image containing an organ within a torso of the body without information from the anatomic image.

12. The system of claim 10, wherein the regularization is performed adaptively based on the organ to which each voxel is assigned.

13. The system of claim 10, further comprising applying respectively different kinetic models to voxels assigned to respectively different ones of the plurality of organs.

14. A non-transitory, machine-readable storage medium containing instructions, such that when a processor executes the instructions, the instructions configure the processor for reconstructing medical images by:
identifying a plurality of organs in a body of a subject based on an anatomic image;
assigning a plurality of voxels in the body to respective ones of the plurality of organs based on the anatomic image; and
reconstructing activity images of the body using respectively different processing for the voxels assigned to each respective one of the plurality of organs, wherein the reconstructing includes performing regularization for one or more selected organs based on information from the anatomic image and wherein the selected organs are selected based on a correlation between voxel values of the anatomic image and voxel values of the activity images.

15. The non-transitory, machine-readable storage medium of claim 14, wherein the anatomic image is a CT image, the activity images are PET images, and the reconstructing includes:
using information from the anatomic image to reconstruct a portion of the anatomic image containing a brain; and
reconstructing a portion of the image containing an organ within a torso of the body without information from the anatomic image.

16. The non-transitory, machine-readable storage medium of claim 14, further comprising instructions for applying respectively different kinetic models to voxels assigned to respectively different ones of the plurality of organs.

* * * * *